(12) United States Patent
Minato

(10) Patent No.: US 7,264,614 B2
(45) Date of Patent: Sep. 4, 2007

(54) DISPOSABLE DIAPER HAVING FOLDING GUIDES FOR IMPROVED FIT

(75) Inventor: Hironao Minato, Kagawa-ken (JP)

(73) Assignee: Uni-Charm Corporation, Ehime-ken (JP)

( * ) Notice: Subject to any disclaimer, the term of this patent is extended or adjusted under 35 U.S.C. 154(b) by 248 days.

(21) Appl. No.: 10/390,171

(22) Filed: Mar. 18, 2003

(65) Prior Publication Data

US 2004/0006325 A1 Jan. 8, 2004

(30) Foreign Application Priority Data

Mar. 20, 2002 (JP) .............................. 2002-079390

(51) Int. Cl.
*A61F 13/15* (2006.01)
*A61F 13/20* (2006.01)

(52) U.S. Cl. .............................. 604/385.01; 604/385.04

(58) Field of Classification Search ........... 604/385.01, 604/385.28, 385.21, 378–383, 358–402, 604/385.03–385.04
See application file for complete search history.

(56) References Cited

U.S. PATENT DOCUMENTS

| | | | |
|---|---|---|---|
| 4,642,110 A | 2/1987 | Dudek | |
| 4,735,624 A * | 4/1988 | Mazars | 604/378 |
| 4,887,602 A * | 12/1989 | O'Leary | 604/385.25 |
| 5,188,627 A * | 2/1993 | Igaue et al. | 604/385.27 |
| 5,197,959 A * | 3/1993 | Buell | 604/385.23 |
| 5,382,246 A * | 1/1995 | Kawano | 604/385.24 |
| 5,601,544 A * | 2/1997 | Glaug et al. | 604/385.28 |
| 5,676,661 A * | 10/1997 | Faulks et al. | 604/385.21 |
| 5,713,883 A * | 2/1998 | Hsieh | 604/385.01 |
| 5,846,231 A * | 12/1998 | Fujioka et al. | 604/380 |
| 5,858,012 A * | 1/1999 | Yamaki et al. | 604/385.27 |
| 6,160,197 A * | 12/2000 | Lassen et al. | 604/358 |
| 6,563,013 B1* | 5/2003 | Murota | 604/380 |
| 6,700,034 B1* | 3/2004 | Lindsay et al. | 604/378 |
| 2002/0065499 A1* | 5/2002 | Ohashi et al. | 604/379 |
| 2002/0123732 A1* | 9/2002 | Koyama et al. | 604/385.24 |
| 2004/0210204 A1* | 10/2004 | Shimada et al. | 604/385.01 |
| 2004/0243081 A1* | 12/2004 | Suzuki et al. | 604/378 |

FOREIGN PATENT DOCUMENTS

| | | |
|---|---|---|
| EP | 1 219 273 A2 | 7/2002 |
| JP | 2002-11047 | 1/2002 |

OTHER PUBLICATIONS

Examiner's markup of O'Leary (US 4887602) Figure 1.*
Definitions of "portion" and "zone" from various online dictionaries, accessed Dec. 17, 2005.*

* cited by examiner

*Primary Examiner*—Michele Kidwell
(74) *Attorney, Agent, or Firm*—Lowe, Hauptman, Ham & Berner, LLP.

(57) ABSTRACT

A disposable diaper includes a liquid-pervious topsheet, a liquid-impervious backsheet and a liquid-absorbent panel interposed between these sheets. Folding guides which are extending in a longitudinal direction are formed between front waist section and wings of the panel and stretchable elastic members which are extending in the longitudinal direction and spaced outward from the folding guides in a transverse direction are contractibly attached to side flaps.

20 Claims, 8 Drawing Sheets

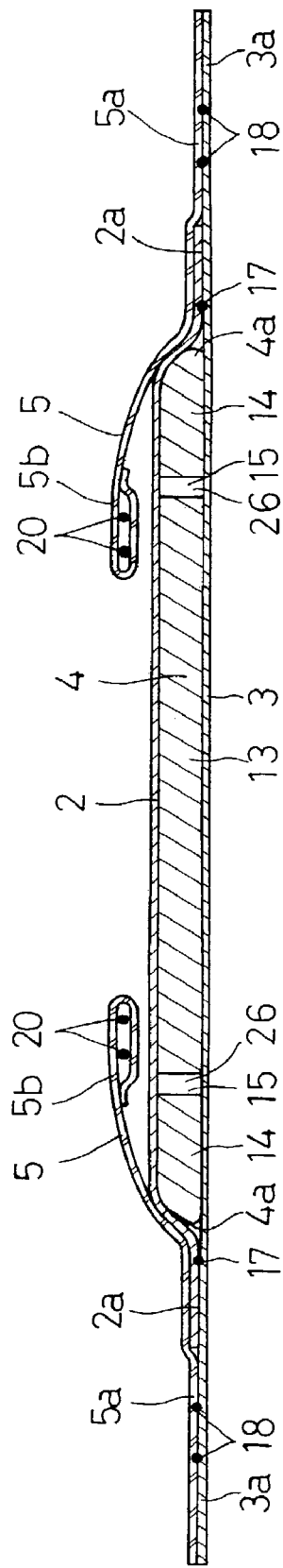

DISPOSABLE DIAPER HAVING FOLDING GUIDES FOR IMPROVED FIT

BACKGROUND OF THE INVENTION

This invention relates to a disposable diaper for absorption and containment of bodily discharges.

Japanese Patent Application No. 2002-11047A discloses an open-type disposable diaper made of a liquid-pervious topsheet, a liquid-impervious backsheet and a liquid-absorbent panel intermediated between these sheets so as to configure, in a longitudinal direction, a front waist region, a rear waist region and a crotch region extending between these two waist regions. The panel is provided with a pair of side flaps extending in the longitudinal direction outside transversely opposite side edges of the panel and with a pair of end flaps extending in a transverse direction outside longitudinally opposite ends of the panel. The diaper presents a substantially hourglass-like planar shape as the diaper is developed in a flat state.

The panel extends over the crotch region into the front and rear waist regions and is hourglass-shaped like the developed diaper. The panel is composed of front and rear sections extending in transversely middle zones of the front and rear waist regions so as to be associated with these front and rear waist regions, respectively, a crotch section extending in a transversely middle zone of the crotch region so as to be associated with the crotch region and a pair of wings extending transversely outward from the front and rear sections. The panel is a mixture of fluff pulp, super-absorbent polymer particles and thermoplastic synthetic resin fibers, entirely compressed to a desired thickness. As a result, stiffness of the panel is higher than that of the top- and backsheets.

To wear this diaper, the side flaps of the rear waist region may be placed upon the outer surfaces of the side flaps of the front waist region and then a pair of tape fasteners attached to the side flaps of the rear waist region may be anchored on the outer surface of the front waist region to connect the front and rear waist regions with each other. With the front and rear waist regions connected with each other, the diaper defines a waist-hole and a pair of leg-holes.

In the case of the diaper disclosed by the above-cited Application, the front and rear waist regions connected with each other in order to be put on the wearer's body certainly form an annulus fully surrounding the wearer's torso. However, the wings of the panel being having a stiffness higher than that of the top- and backsheets can not be smoothly bent in conformity with the contour of the wearer's torso. In other words, it is difficult to bring the wings in close contact with the wearer's torso. In this well-known diaper, it is likely that a gap might be left between the wings of the panel and the wearer's body and a bodily discharge absorbing capacity expected for these wings could not be fully utilized.

SUMMARY OF THE INVENTION

It is an object of this invention to provide a disposable diaper improved so that the wings of the panel can be reliably brought in close contact with the wearer's torso as the diaper is put on the wearer's body and in this way the bodily discharge absorbing capacity expected for these wings can be fully utilized.

In accordance with this invention, there is provided a disposable diaper comprising a liquid-pervious topsheet, a liquid-impervious backsheet and a liquid-absorbent panel interposed between these sheets so as to configure, in a longitudinal direction, a front waist region, a rear waist region and a crotch region extending between these waist regions, a pair of side flaps extending in the longitudinal direction outside transversely opposite side edges of the panel and a pair of end flaps extending in a transverse direction outside longitudinally opposite ends of the panel. The panel has front and rear waist sections lying in transversely middle zones of the front and rear waist regions, respectively, a crotch section lying in a transversely middle zone of the crotch region and a pair of wings extending outward from at least one of the front and rear waist sections in the transverse direction.

The disposable diaper according to this invention further comprises folding guides which are extending in the longitudinal direction and defined between the waist sections and respective the wings of the panel and stretchable elastic members which are extending in the longitudinal direction, spaced outwardly from the folding guides in the transverse direction by a given dimension and contractibly attached to the side flaps.

This invention includes the following embodiments. Longitudinal ends of the elastic members are secured to the wings.

The folding guides are defined by panel-free zones and extend from inner ends of the wings put aside toward the crotch region to outer ends of the wings put aside toward the end flaps.

The folding guides are defined by low stiffness zones of the panel, i.e., zones having a stiffness lower than a stiffness in other zones of the panel and extend from the inner ends of the wings put aside toward the crotch region to the outer ends of the wings put aside toward the end flaps.

The folding guides are defined by slits in the panel and extend from the inner ends of the wings put aside toward the crotch region to the outer ends of the wings put aside toward the end flaps.

BRIEF DESCRIPTION OF THE DRAWINGS

FIG. 8 is a sectional view taken along a line C-C in FIG. 7.

DETAILED DESCRIPTION OF THE PREFERRED EMBODIMENTS

Details of the disposable diaper according to this invention will be more fully understood from the description given hereunder in reference to the accompanying drawings.

Figure 1:
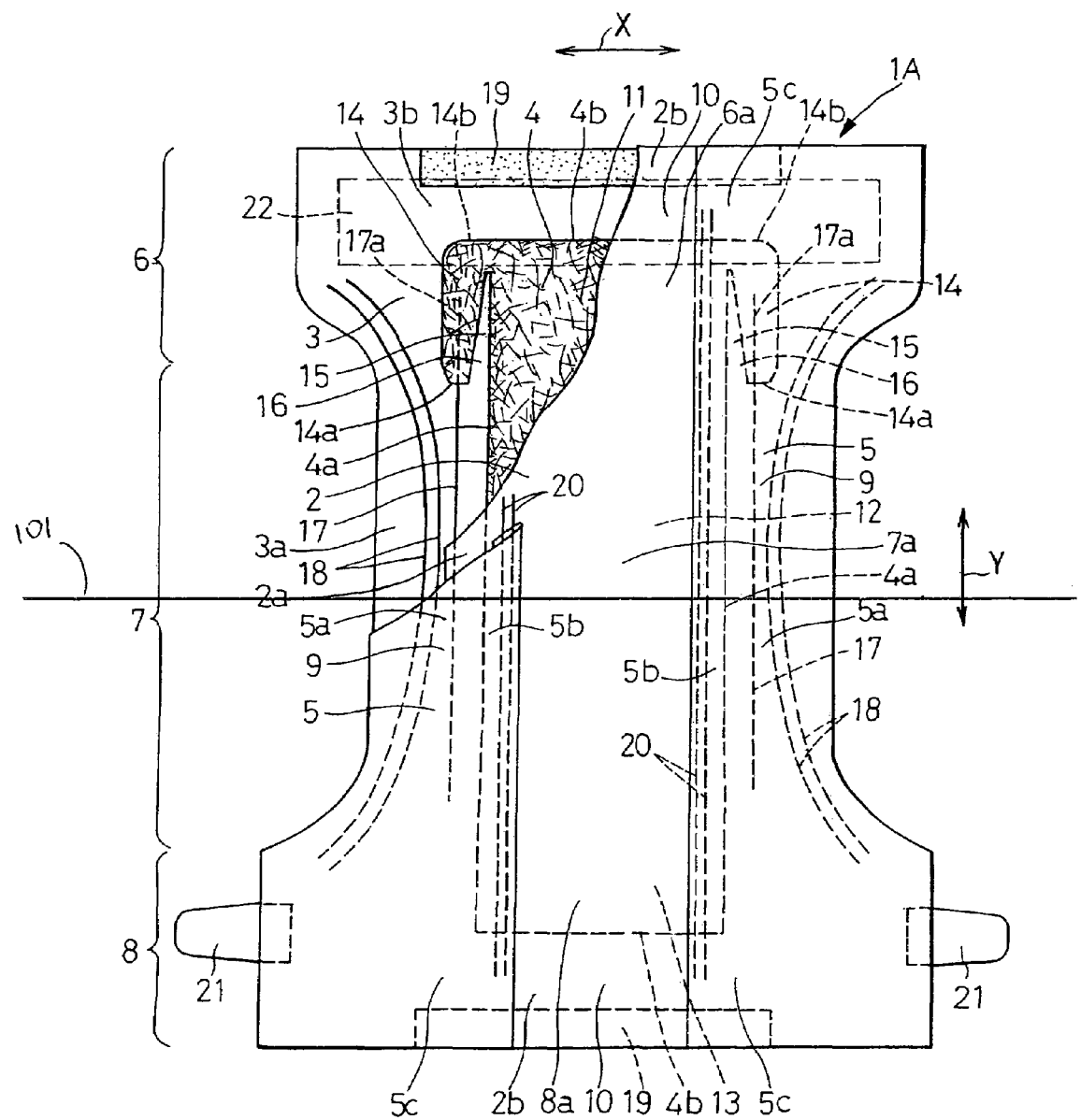
FIG. 1 is a partially cutaway plan view showing the diaper according to this invention.
Figure 2:
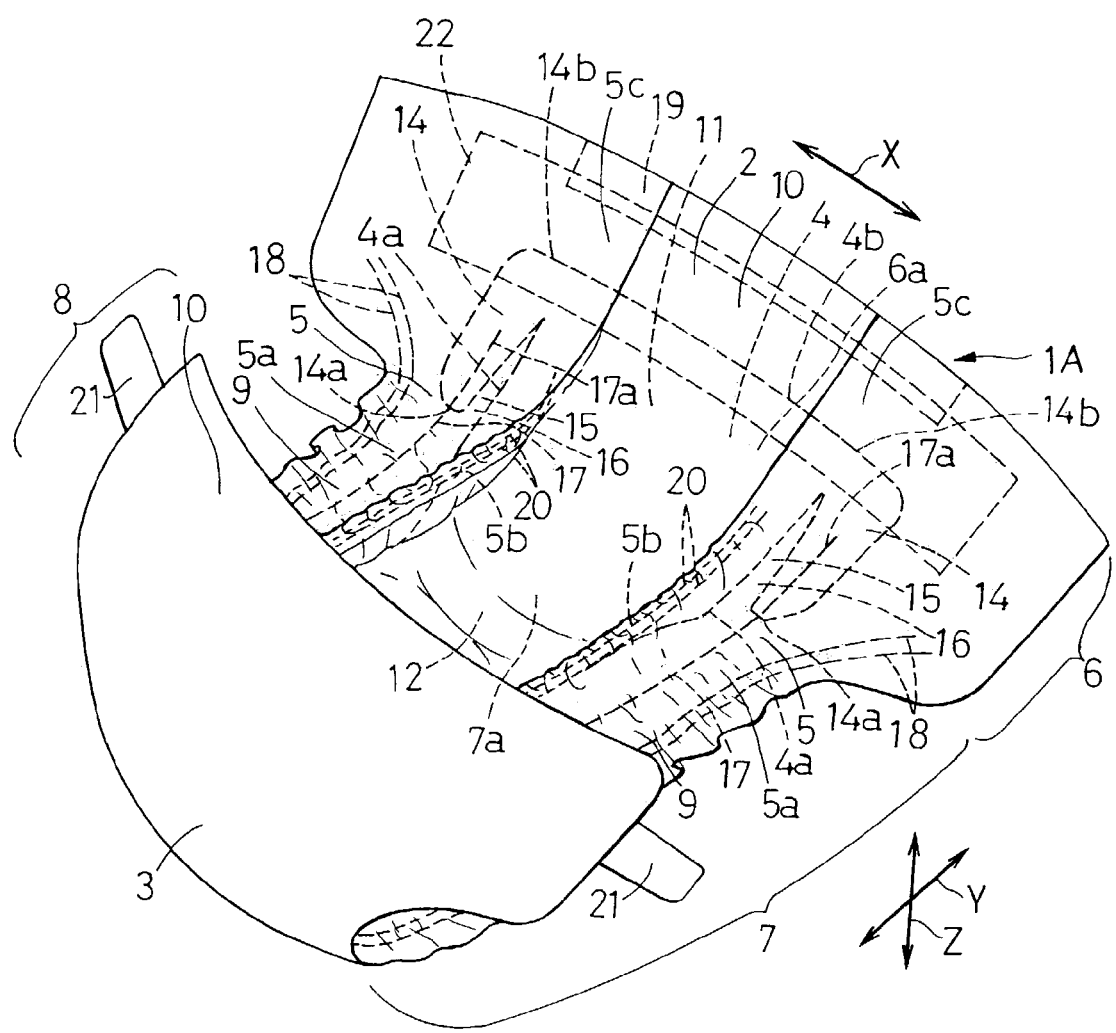
FIG. 2 is a perspective view showing the diaper of FIG. 1.
Figure 3:
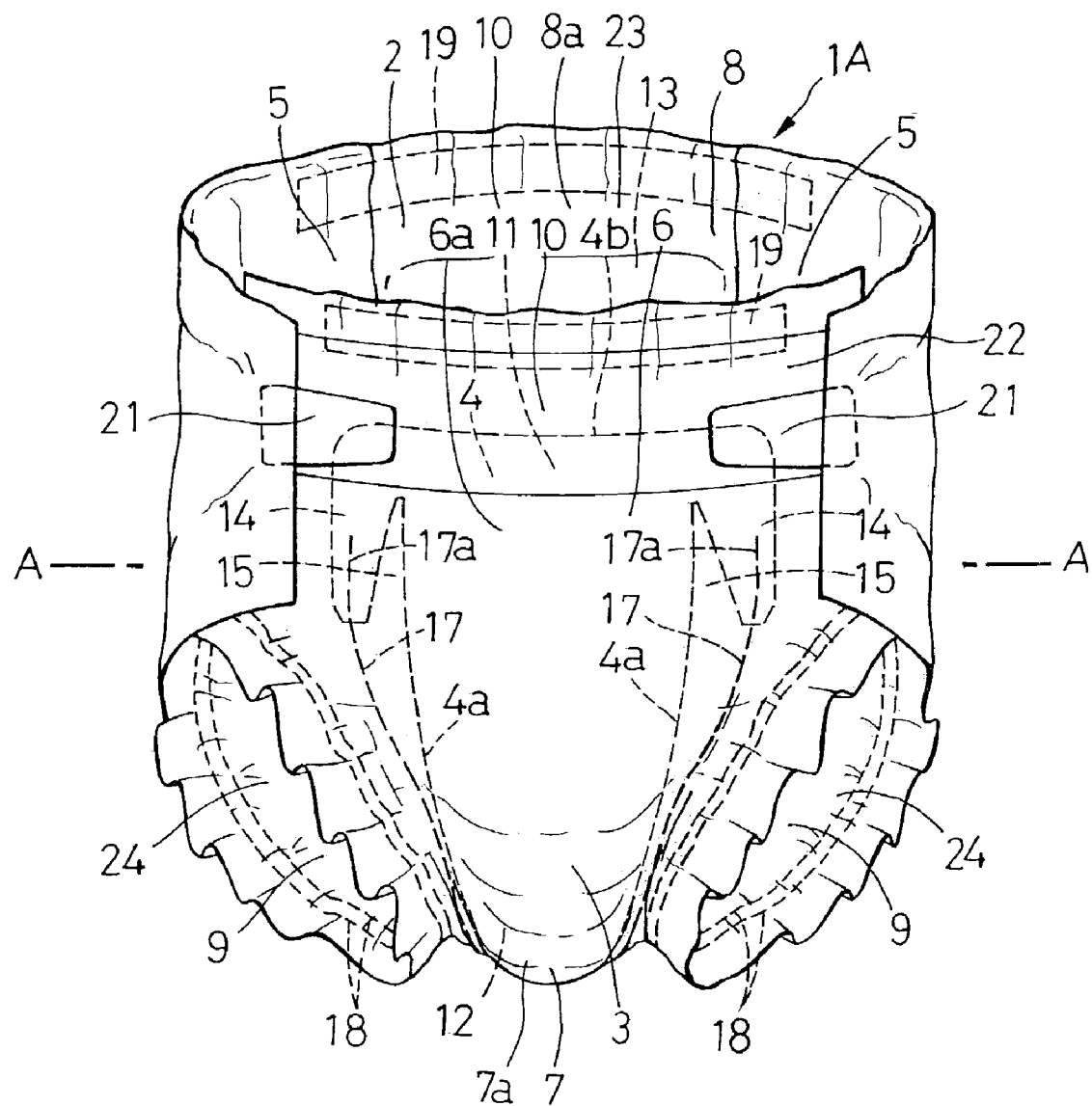
FIG. 3 is a perspective view showing the diaper of FIG. 1 as put on a wearer's body.
Figure 4:
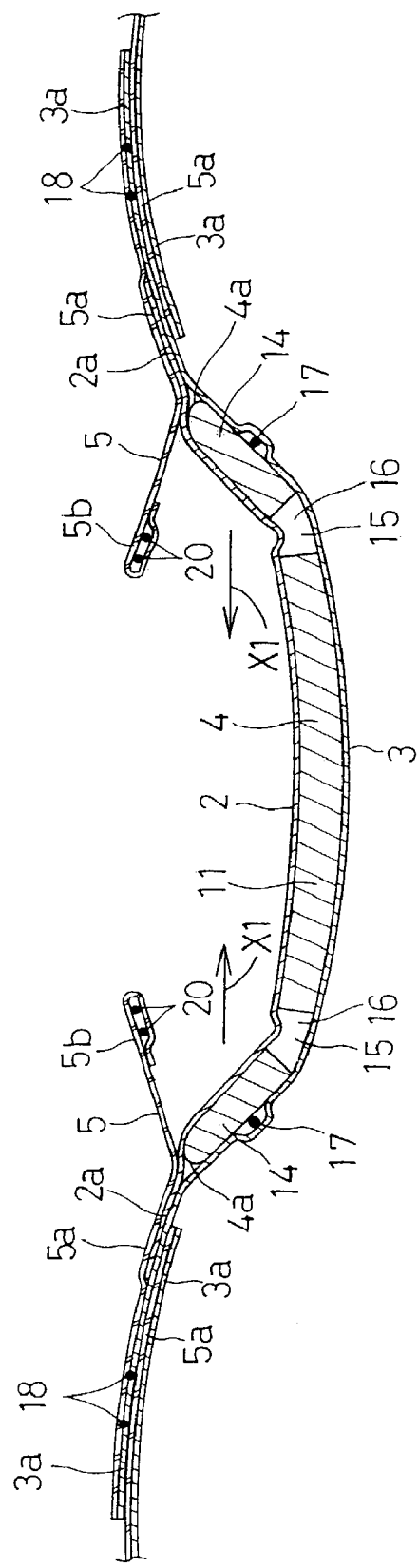
FIG. 4 is a sectional view taken along a line A-A in FIG. 3.

FIG. 1 is a partially cutaway plan view showing the diaper 1A according to this invention, FIG. 2 is a perspective view showing the diaper 1A of FIG. 1, FIG. 3 is a perspective view showing the diaper 1A of FIG. 1 as put on a wearer's body and FIG. 4 is a sectional view taken along a line A-A in FIG. 3. In FIGS. 1 and 2, a transverse direction is indicated by an arrow X, a longitudinal direction is indicated by an arrow Y and a thickness direction is indicated by an arrow Z. Designation "inner surfaces of top- and backsheets 2, 3 and leak-barrier sheets 5" should be understood to be the surfaces thereof facing a panel 4 and designation "outer surfaces of these sheets 2, 3, 5 should be understood to be the surfaces facing away from the panel 4. Designation "upper surface of the panel 4" should be understood to be the surface facing the topsheet 2 and designation "lower surface of the panel 4" should be understood to be the surface facing the backsheet 3.

The diaper 1A comprises a liquid-pervious topsheet 2 facing a wearer's body, a liquid-impervious backsheet 3 facing away from the wearer's body and the liquid-absorbent panel 4 interposed between the top- and backsheets 2, 3 and firmly bonded to the inner surface of at least one of these sheets 2, 3. In addition to the top- and backsheets 2, 3 and the panel 4, the diaper 1A comprises liquid-impervious leak-barrier sheets 5 lying on the outer surface of the topsheet 2.

The diaper 1A is composed of, as viewed in its longitudinal direction, a front waist region 6, a rear waist region 8 and a crotch region 7 extending between these waist regions 6, 8 and, in addition, a pair of side flaps 9 extending in the longitudinal direction outside transversely opposite side edges 4a of the panel 4 and a pair of end flaps 10 extending in the transverse direction outside longitudinally opposite ends 4b of the panel 4. In the crotch region 7, the side flaps 9 of the diaper 1A curve inwardly as viewed in the transverse direction of the diaper 1A so that the diaper 1A presents an hourglass-like planar shape. The diaper 1A is of the open-type having its front and rear waist regions 6, 8 adapted to be connected to each other when the diaper 1A is put on the wearer's body.

The panel 4 extends over the crotch region 7 into the front and rear waist regions 6, 8. The panel 4 has front and rear waist sections 11, 13 lying in transversely middle zones 6a, 8a of the front and rear waist regions 6, 8, respectively, a crotch section 12 lying in a transversely middle zone 7a of the crotch region 7 and a pair of wings 14 extending outwardly from the front waist section 11 in the transverse direction. A pair of folding guides 15 extending in the longitudinal direction are defined between the front waist section 11 and the respective wings 14 of the panel 4.

The panel 4 is a mixture of fluff pulp and super-absorbent polymer particles or a mixture of fluff pulp, super-absorbent polymer particles and thermoplastic synthetic resin fibers, in either case, compressed to a desired thickness. Accordingly, the panel 4 has a stiffness higher than that of the top- and backsheets 2, 3. Preferably, the panel 4 is entirely covered with a liquid-pervious sheet such as a tissue paper or a hydrophilic fibrous nonwoven fabric in order to prevent the panel 4 from getting out of its initial shape or to avoid falling off of the polymer particles from the panel 4.

The folding guides 15 are defined by panel-free zones 16. Each of these folding guides 15 extends from an inner end 14a of the associated wing 14 put aside toward the crotch region 7 to an outer end 14b of the associated wing 14 put aside toward the associated end flap 10. Each of these folding guides 15 is tapered from the inner end 14a toward the outer end 14b substantially in a triangle.

In the crotch region 7, each of the side flaps 9 is provided with a single stretchable elastic member 17 rectilinearly extending in the longitudinal direction. These elastic members 17 lie outside the respective side edges 4a of the crotch section 12 and spaced outwardly from the respective folding guides 15 in the transverse direction by a given dimension. The elastic member 17 is contractibly attached to the associated side flap 9 and its one longitudinal end portion 17a is connected to the associated wing 14 in the vicinity of the inner end 14a thereof. The folding guide 15 is spaced from the elastic member 17 preferably by 1-30 mm.

In the crotch region 7, a plurality of leg-surrounding elastic members 18 extending in the longitudinal direction are contractibly attached to each of the side flaps 9 so as to be spaced outwardly from the elastic member 17 in the transverse direction by a given dimension. The leg-surrounding elastic members 18 curve toward the transversely middle zone 7a of the crotch region 7 so as to describe substantially circular arcs. The end flaps 10 are respectively provided with band-like waist-surrounding elastic members 19 extending in the transverse direction and contractibly attached thereto.

The leak-barrier sheets 5 are attached to the respective side flaps 9 and extend over the crotch region 7 into the front and rear waist regions 6, 8. Each of these leak-barrier sheets has a fixed lateral portion 5a extending in the longitudinal direction, a free lateral portion 5b extending in the longitudinal direction and normally biased to rise above the topsheet 2 and fixed longitudinally opposite end portions 5c collapsed inwardly in the transverse direction of the diaper 1A and fixed in such a collapsed state. The free lateral portion 5b is provided with a stretchable elastic member 20 extending in the longitudinal direction and contractibly attached thereto. The elastic member 20 is wrapped with a part of the free lateral portion 5b.

The side flaps 9 are formed by transversely opposite lateral portions 2a, 3a of the top- and backsheets 2, 3 extending outwardly from the side edges 4a of the panel 4 in the transverse direction and the fixed lateral portions 5a of the leak-barrier sheets 5. In the side flaps 9, the lateral portions 2a of the topsheet 2 extend outwardly slightly beyond the side edges 4a of the panel 4 in the transverse direction and the lateral portions 3a of the backsheet 3 as well as the fixed lateral portions 5a of the leak-barrier sheets 5 extend outwardly beyond the lateral portions 2a of the topsheet 2 in the transverse direction. The lateral portions 2a are interposed between the lateral portions 3a and the lateral portions 5a and bonded to the inner surfaces of these lateral portions 3a, 5a. The lateral portions 3a overlap the lateral portions 5a and have inner surfaces bonded together in these overlapping zones.

The elastic members 17 are respectively interposed between the lateral portions 2a of the topsheet 2 and the lateral portions 3a of the backsheet 3 and bonded to the inner surfaces of these lateral portions 2a, 3a of the top- and backsheets 2, 3. Each of these elastic members 17 has its longitudinal one end portion 17a interposed between the backsheet 3 and the panel 4 and bonded to the inner surface of the backsheet 3 and the lower surface of the panel 4. The leg-surrounding elastic members 18 are interposed between the lateral portions 3a of the backsheet 3 and the fixed lateral portions 5a of the leak-barrier sheets 5 and bonded to the inner surfaces of the lateral portions 3a, 5a of these sheets 3, 5.

The end flaps 10 are formed by longitudinally opposite end portions 2b, 3b of the top- and backsheets 2, 3 extending outwardly beyond the longitudinally opposite ends 4b of the panel 4 in the longitudinal direction. In these end flaps 10, the top- and backsheets 2, 3 are overlaid and joined together at the end portions 2b, 3b. The waist-surrounding elastic members 19 are interposed between the end portions 2b of the topsheet 2 and the end portions 3b of the backsheet 3 and bonded to the inner surfaces of these ends 2b, 3b of these sheets 2, 3. The fixed end portions 5c of the respective leak-barrier sheets 5 are bonded to the outer surfaces of the end portions 2b of the topsheet 2.

The rear waist region 8 is provided with a pair of tape fasteners 21 respectively extending outwardly in the transverse direction from the side flaps 9. The tape fasteners 21 have free end portions coated with a self-adhesive (not shown). In the front waist region 6, the backsheet 3 is provided on its outer surface with a target tape 22 which is relatively long in the transverse direction so that the tape fasteners 21 may be detachably anchored thereon. The tape fasteners 21 and the target tape 22 are made of flexible plastic film.

As can be seen in FIG. 1, wings 14 and the respective folding guides 15 are elongated in the longitudinal direction Y of diaper 1A, but do not extend beyond a transverse center line 101 that bisects an entire longitudinal dimension of diaper 1A. In addition, an entire width of the crotch region 7 in the vicinity of center line 101 is free of both wings 14 and folding guides 15.

To put the diaper 1A on the wearer's body, the side flaps 9 in the rear waist region 8 may be placed on the outer surfaces of the side flaps 9 in the front waist region 6 and then the free end portions of the respective tape fasteners 21 may be anchored on the target tape 22 by means of the self-adhesives to connect the front and rear waist regions 6, 8 to each other. With the front and rear waist regions 6, 8 connected to each other in this manner, the diaper 1A defines a waist-hole 23 and a pair of leg-holes 24. With the diaper 1A put on the wearer's body, the front and rear waist sections 11, 13 of the panel 4 are closely placed against the wearer's torso through the topsheet 2 and the crotch section 12 of the panel 4 is closely placed against the wearer's crotch region through the topsheet 2.

In the diaper 1A put on the wearer's body, the crotch region 7 is squeezed by the wearer's crotch and consequently the elastic members 17 are drawn toward the transversely middle zone 7a of the crotch region 7, as shown in FIG. 3. As a result, the respective elastic members 17 obliquely extend from the upper ends 17a toward the crotch region 7 so that the elastic members 17 get nearer to the transversely middle zone 7a of the crotch region 7.

The front and rear waist regions 6, 8 cooperate to form an annulus and a force generated thereby is exerted upon the wings 14 of the panel 4 to fold them as the diaper 1A is put on the wearer's body. Simultaneously, a contractile force of the elastic members 17 generated in the longitudinally middle zones thereof is exerted from the respective longitudinal ends 17a upon the transversely middle zone 7a of the crotch region 7 so that the wings 14 of the panel 4 may be drawn inwardly in the transverse direction of the diaper 1A. As indicated by an arrow X1 in FIG. 4, the force intending to bend the wings 14 cooperates with the contractile force of the elastic members 17 to fold inwardly the wings 14 of the panel 4 along the respective folding guides 15 in the transverse direction of the diaper 1A.

The wings 14 of the panel 4 are folded inwardly in the transverse direction of the diaper 1A as the diaper 1A is put on the wearer's body. With an advantageous consequence, the wings 14 can be reliably brought in close contact with the wearer's torso without leaving any gap between the wings 14 and the wearer's torso. In this way, the bodily discharge absorbing capacity expected for these wings 14 can be fully utilized.

In the diaper 1A, the folding guides 15 are defined by panel-free zones 16 and therefore the wings 14 can be easily folded along the respective folding guides 15 which are substantially free from affection by the high stiffness of the panel 4.

The elastic members 20 contract in the longitudinal direction and thereby cause the free lateral portions 5b of the leak-barrier sheets 5 to rise above the topsheet 2 as the diaper 1A curves in the longitudinal direction with the topsheet 2 inside as shown in FIG. 2. In the diaper 1A, the free lateral portions 5b of the respective leak-barrier sheets 5 form barriers against leakage of bodily discharges and prevent bodily discharges from leaking sideways beyond the side flaps 9.

Figure 5:
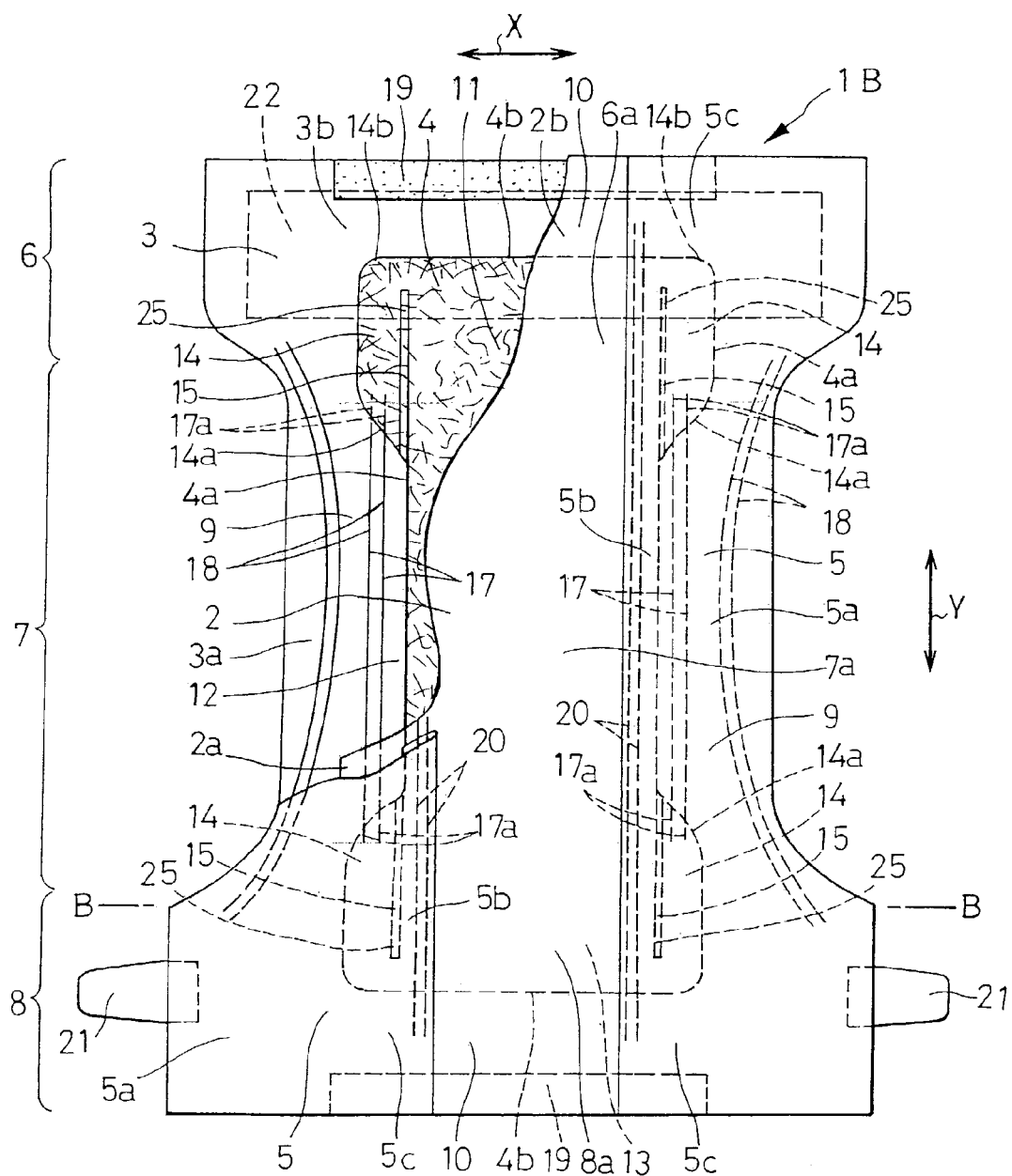
FIG. 5 is a partially cutaway plan view showing one preferred embodiment of the diaper according to this invention.
Figure 6:
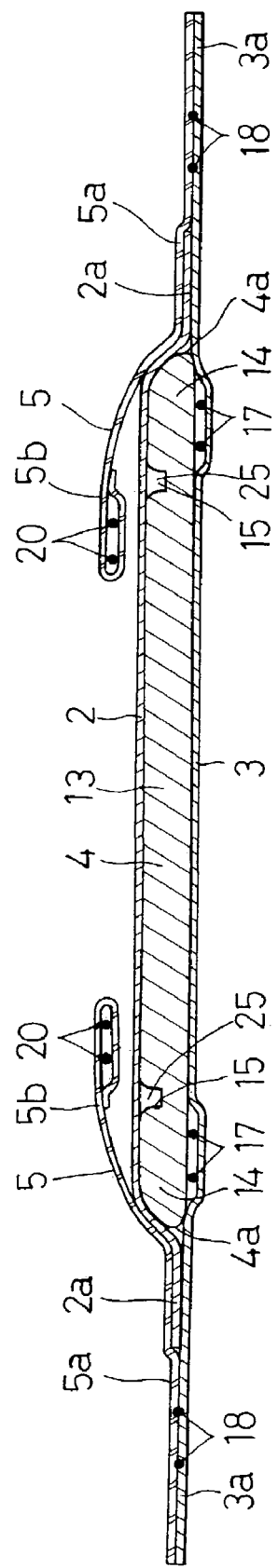
FIG. 6 is a sectional view taken along a line B-B in FIG. 5.

FIG. 5 is a partially cutaway plan view showing one preferred embodiment 1B of the diaper according to this invention and FIG. 6 is a sectional view taken along a line B-B in FIG. 5. In FIG. 5, the transverse direction is indicated by the arrow X and the longitudinal direction is indicated by the arrow Y.

The diaper 1B is of open-type characterized in that the front and rear waist regions 6, 8 are connected to each other immediately before actual use of the diaper 1B. Basically, the diaper 1B comprises a liquid-pervious topsheet 2, a liquid-impervious backsheet 3 and a liquid-absorbent panel 4 interposed between the top- and backsheets 2, 3. The diaper 1B further comprises a pair of side flaps 9 and a pair of end flaps 10. The side flaps 9 are provided with liquid-impervious leak-barrier sheets 5 attached thereto.

The panel 4 has front and rear waist sections 11, 13 lying in transversely middle zones 6a, 8a of the front and rear waist regions 6, 8, respectively, a crotch section 12 lying in a transversely middle zone 7a of the crotch region 7 and a pair of wings 14 extending outwardly from the front and rear waist sections 11, 13 in the transverse direction. The panel 4 has an hourglass-shape like the planar shape of the diaper 1B. A pair of folding guides 15 extending in the longitudinal direction are defined between the front and rear waist sections 11, 13 and the respective wings 14 of the panel 4.

The folding guides 15 are defined by low stiffness zones 25 of the panel 4, i.e., zones having a stiffness lower than stiffness in the other zone of the panel 4. Each of these folding guides 15 extends from the inner end 14a to the vicinity of the outer end 14b of the associated wing 14. In these folding guides 15, at least one of the super-absorbent polymer particles and the thermoplastic synthetic resin fiber making a part of the panel 4 has a basis weight per unit volume smaller than that per unit volume in the zone of the panel 4 except for the folding guides 15 and the panel 4 has its thickness smaller in these folding guides 15 than in the zone of the panel 4 except for the folding guides 15.

In the crotch region 7, each of the side flaps 9 is provided with a plurality of stretchable elastic members 17 rectilinearly extending in the longitudinal direction. These elastic members 17 lie outside the respective side edges 4a of the crotch section 12 and spaced outwardly from the respective folding guides 15 in the transverse direction by a given dimension. The elastic members 17 are contractibly attached to the side flap 9 and the longitudinal end portions 17a is connected to the wings 14 in the vicinity of the inner ends 14a thereof. The folding guide 15 is spaced from the elastic member 17 preferably by the same dimension as in the case of FIG. 1.

In the crotch region 7, a plurality of leg-surrounding elastic members 18 extending in the longitudinal direction are contractibly attached to each of the side flaps 9 so as to be spaced outwardly from the elastic members 17 in the transverse direction by a given dimension. The end flaps 10 are respectively provided with band-like waist-surrounding elastic members 19 extending in the transverse direction and contractibly attached thereto.

In the diaper 1B put on the wearer's body, the respective elastic members 17 obliquely extend from the longitudinal end portions 17a toward the crotch region 7 so that the elastic members 17 get nearer to the transversely middle zone 7a of the crotch region 7. In the diaper 1B, the front and rear waist regions 6, 8 cooperate to form an annulus and a force generated thereby is exerted upon the wings 14 of the panel 4 to fold them. And simultaneously, a contractile force of the elastic members 17 is exerted from the respective longitudinal end portions 17a upon the transversely middle zone 7a of the crotch region 7 so that the wings 14 of the panel 4 may be drawn inwardly in the transverse direction of the diaper 1B and the wings 14 are folded inwardly along the respective folding guides 15 in the transverse direction of the diaper 1B. In the diaper 1B, the wings 14 can be reliably brought in close contact with the wearer's torso without leaving any gap between the wings 14 and the wearer's torso. In this way, the bodily discharge absorbing capacity expected for these wings 14 can be fully utilized.

In the diaper 1B, the folding guides 15 are defined by the low stiffness zones 25 provided within the panel 4 and therefore the wings 14 can be easily folded along the respective folding guides 15 which are substantially free from affection by the high stiffness of the panel 4.

Figure 7:
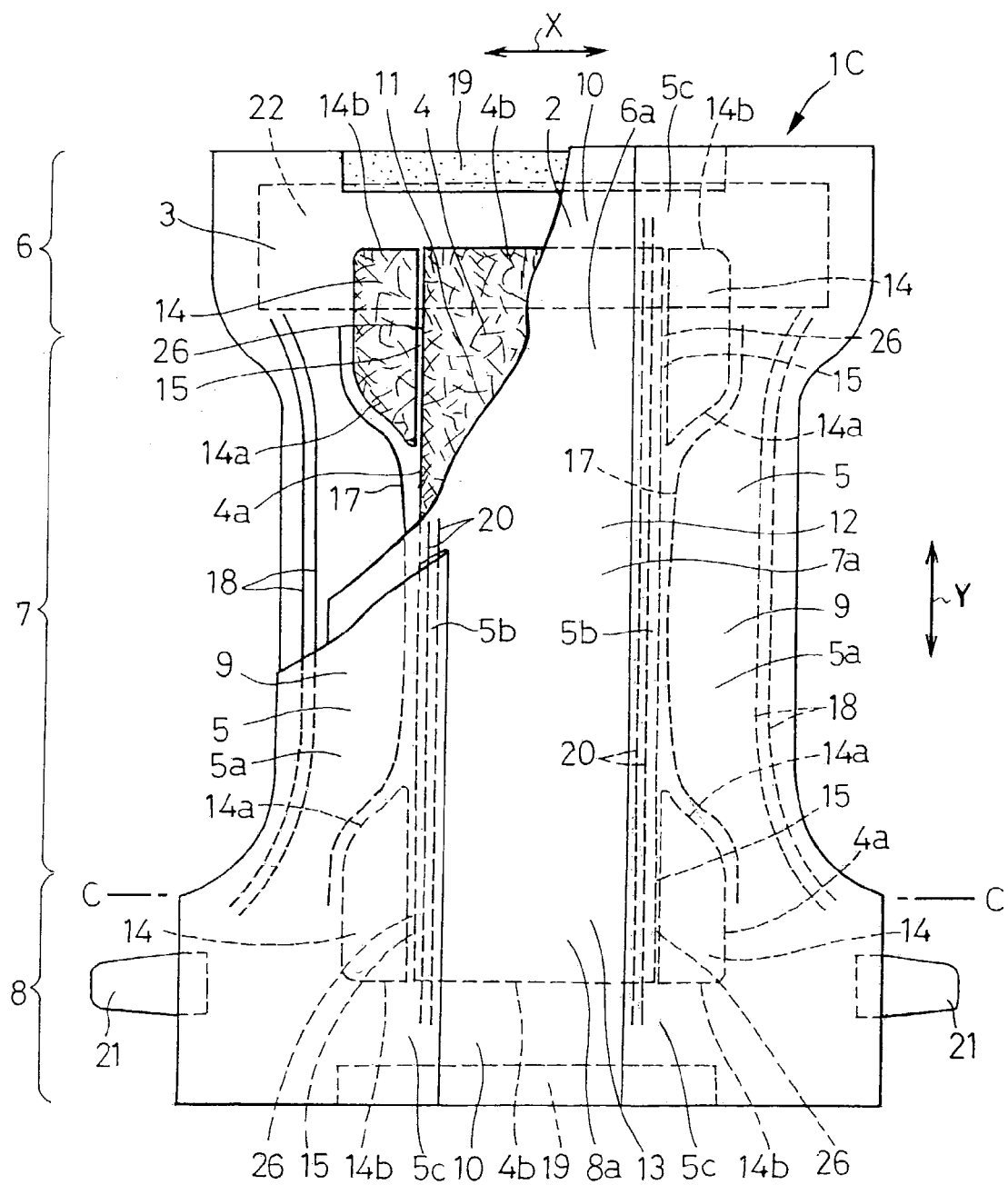
FIG. 7 is a partially cutaway plan view showing another preferred embodiment of the diaper according to this invention.

FIG. 7 is a partially cutaway plan view showing another preferred embodiment 1C of the diaper according to this invention and FIG. 8 is a sectional view taken along a line C-C in FIG. 7. In FIG. 7, the transverse direction is indicated by the arrow X and the longitudinal direction is indicated by the arrow Y.

The diaper 1C is of open-type characterized in that the front and rear waist regions 6, 8 are connected to each other immediately before its actual use. Basically, the diaper 1C comprises a liquid-pervious topsheet 2, a liquid-impervious backsheet 3 and a liquid-absorbent panel 4 interposed between the top- and backsheets 2, 3. The diaper 1C further comprises a pair of side flaps 9 and the pair of end flaps 10 wherein the side flaps 9 are provided with the liquid-impervious leak-barrier sheets 5 attached thereto.

The panel 4 has front and rear waist sections 11, 13 lying in transversely middle zones 6a, 8a of the front and rear waist regions 6, 8, respectively, a crotch section 12 lying in a transversely middle zone 7a of the crotch region 7 and a pair of wings 14 extending outwardly from the front and rear waist sections 11, 13 in the transverse direction. The panel 4 has an hourglass-shape like the planar shape of the diaper 1C. A pair of folding guides 15 extending in the longitudinal direction are defined between the front and rear waist sections 11, 13 and the respective wings 14 of the panel 4.

The folding guides 15 are defined by slits 26 in the panel 4. The folding guides 15 fully extend in the longitudinal direction from the inner ends 14a to the outer ends 14b of the respective wings 14 so that the front and rear waist sections 11, 13 and the wings 14 are interrupted by the respective folding guides 15.

In the crotch region 7, each of the side flaps 9 is provided with a single stretchable elastic member 17 rectilinearly extending in the longitudinal direction. The elastic members 17 lie outside the respective side edges 4a of the crotch section 12 and spaced outwardly from the respective folding guides 15 in the transverse direction by a given dimension. The elastic members 17 are contractibly attached to the side flap 9. These elastic members 17 curve toward the transversely middle zone 7a of the crotch region 7. Each of the folding guides 15 is spaced from the associated elastic member 17 preferably by the same dimension as in the case of FIG. 1.

In the crotch region 7, a plurality of leg-surrounding elastic members 18 extending in the longitudinal direction are contractibly attached to each of the side flaps 9 so as to be spaced outwardly from the elastic members 17 in the transverse direction by a given dimension. The end flaps 10 are respectively provided with band-like waist-surrounding elastic members 19 extending in the transverse direction and contractibly attached thereto.

In the diaper 1C put on the wearer's body, the respective elastic members 17 obliquely extend from the longitudinal end portions 17a toward the crotch region 7 so that the elastic members 17 get nearer to the transversely middle zone 7a of the crotch region 7. In the diaper 1C, the front and rear waist regions 6, 8 cooperate to form an annulus and a force generated thereby is exerted upon the wings 14 of the panel 4 to fold them. And simultaneously, a contractile force of the elastic members 17 is exerted from the respective longitudinal end portions 17a upon the transversely middle zone 7a of the crotch region 7 so that the wings 14 of the panel 4 may be drawn inwardly in the transverse direction of the diaper 1C and the wings 14 are folded inwardly along the respective folding guides 15 in the transverse direction of the diaper 1C. In the diaper 1C, the wings 14 can be reliably brought in close contact with the wearer's torso without leaving any gap between the wings 14 and the wearer's torso. In this way, the bodily discharge absorbing capacity expected for these wings 14 can be fully utilized.

In the diaper 1C, the folding guides 15 are defined by the slits in the panel 4 and therefore the folding guides 15 are not affected by relatively high stiffness of the panel 4. In this way, the wings 14 can be easily folded along the folding guides 15.

In the diaper 1C, the elastic members 17 curve toward the transversely middle zone 7a of the crotch region 7. This feature further facilitates the contractile force of the elastic members 17 in the longitudinal direction to be transmitted toward the transversely middle zone 7a of the crotch region 7 and thereby further facilitates the wings 14 of the panel 4 to be drawn inwardly in the transverse direction of the diaper 1C by the contractile force of the elastic members 17.

A stock material for the topsheet 2 may be selected from the group consisting of a hydrophilic fibrous nonwoven fabric, a hydrophobic fibrous nonwoven fabric having a plurality of perforations and a plastic film having a plurality of fine perforations. A stock material for the backsheet 3 and the leak-barrier sheets 5 may be selected from the group consisting of a hydrophobic fibrous nonwoven fabric, a breathable but liquid-impervious plastic film, a composite nonwoven fabric comprising two or more hydrophobic fibrous nonwoven fabric layers laminated one with another and a composite sheet comprising a hydrophobic fibrous nonwoven fabric and a breathable but liquid-impervious plastic film laminated with each other.

It is also possible to use, as a stock material for the backsheet 3 and the leak-barrier sheets 5, a composite nonwoven fabric comprising a melt blown fibrous nonwoven fabric having a high water-resistance and two layers of spun bond fibrous nonwoven fabrics, each having a high strength and a high flexibility, sandwiching the melt blown fibrous nonwoven fabric therebetween.

The type of nonwoven fabric to be used may be selected from the group consisting of spun lace-, needle punch-, melt blown- thermal bond-, spun bond-, chemical bond- and air-through-types. Component fibers of the nonwoven fabric may be selected from the group consisting of polyolefine-, polyester-and polyamide-based fibers, and core-sheath type or side-by-side type conjugated fibers of polyethylene/polypropylene or polyethylene/polyester.

To join the top- and backsheets 2, 3 to each other, to secure the panel 4 to the top- and backsheets 2, 3, to secure the leak-barrier sheets 5 to the top- and backsheets 2, 3 and to secure the elastic members 17, 18, 19, 20 to the sheets 2, 3, 5, hot melt adhesives or welding technique such as a heat-sealing or an ultrasonic sealing may be employed.

In the disposable diaper according to this invention, the folding guides are formed between the front and rear waist sections and the wings of the panel and, in the crotch region, the stretchable elastic members extending in the longitudinal direction and spaced outwardly from the respective folding guides in the transverse direction by a given dimension are contractibly attached to the respective side flaps. The crotch region is squeezed in the crotch of the wearer and the elastic members are drawn toward the transversely middle zone of the crotch region as this diaper is put on the wearer's body. Consequently, the elastic members obliquely extend from the longitudinal ends toward the crotch region so that the elastic members get nearer to the transversely middle zone of the crotch region.

In this diaper, the front and rear waist regions cooperate to form an annulus and a force generated thereby is exerted upon the wings of the panel to fold them. And simultaneously, a contractile force of the elastic members is exerted from the respective longitudinal end portions upon the transversely middle zone of the crotch region so that the wings of the panel may be drawn inwardly in the transverse direction of the diaper and the wings are folded inwardly along the respective folding guides in the transverse direction of the diaper. In this diaper, the wings can be reliably brought in close contact with the wearer's torso without leaving any gap between the wings and the wearer's torso. In this way, the bodily discharge absorbing capacity expected for these wings can be fully utilized.

What is claimed is:

1. A disposable diaper, comprising a liquid-pervious topsheet, a liquid-impervious backsheet and a liquid-absorbent panel interposed between said sheets, said diaper further comprising:
   a front waist region, a rear waist region and a crotch region extending between said waist regions in a longitudinal direction of said diaper,
   a pair of side flaps extending in said longitudinal direction outside transversely opposite side edges of said panel, and
   a pair of end flaps extending in a transverse direction outside longitudinally opposite ends of said panel;
   wherein
   said panel has:
      front and rear sections lying in said front and rear waist regions, respectively,
      a crotch section lying in said crotch region, and connecting said front and rear sections,
      a pair of wings each of which extends in the longitudinal direction from a proximal end to a distal end thereof, said proximal end being contiguous to and extending outwardly from one of transversely opposite sides of at least one of said front and rear sections in said transverse direction, and
      folding guides extending in said longitudinal direction and defined between said at least one of said front and rear sections and the distal ends of respective said wings; and
   said disposable diaper further comprises:
      stretchable elastic members extending in said longitudinal direction, spaced outwardly from said folding guides in said transverse direction by a given dimension and contractibly attached to said side flaps;
   the folding guides are continuous and elongated in the longitudinal direction without extending beyond a transverse center line that bisects an entire longitudinal dimension of said diaper;
   an entire width of the crotch region in a vicinity of said center line is free of both said wings and said folding guides;
   said folding guides are zones devoid of absorbent material of said panel;
   an entire width of each of said zones, as measured in the transverse direction, increases in the longitudinal direction toward said transverse center line; and
   an entire width of each said wing, as measured in the transverse direction, decreases in the longitudinal direction towards said transverse center line.

2. The diaper according to claim 1, wherein longitudinal end portions of said elastic members are directly bonded to respective said wings.

3. The diaper according to claim 2, wherein said elastic members are coexistent with said wings only at said longitudinal end portions.

4. The diaper according to claim 3, wherein middle portions of said elastic members are not located beneath any part of said panel.

5. The diaper according to claim 4, further comprising:
   stretchable leg elastics each extending in said longitudinal direction, entirely spaced outwardly from said panel in said transverse direction and contractibly attached to one of said side flaps;
   wherein an entirety of each of said leg elastics is not located beneath any part of said panel.

6. The diaper according to claim 5, wherein
   the leg elastics attached to the same side flap generally run parallel to each other, but not parallel to the elastic member attached to said same side flap.

7. The diaper according to claim 1, wherein said panel has said wings only in one of said front and rear sections thereof.

8. The diaper according to claim 1, wherein an entire longitudinal extent of each of said wings is less than half of that of said panel.

9. The diaper according to claim 1, further comprising:
   stretchable leg elastics each extending in said longitudinal direction, entirely spaced outwardly from said panel in said transverse direction and contractibly attached to one of said side flaps.

10. The diaper according to claim 9, wherein
    the leg elastics attached to the same side flap generally run parallel to each other, but not parallel to the elastic member attached to said same side flap.

11. The diaper according to claim 10, wherein
    the leg elastics attached to the same side flap define curves that are convex toward the panel, whereas the elastic member attached to said same side flap is generally straight.

12. A disposable diaper, comprising a liquid-pervious topsheet, a liquid-impervious backsheet and a liquid-absorbent panel interposed between said sheets, said diaper further comprising a front waist region, a rear waist region and a crotch region extending between said waist regions in a longitudinal direction of said diaper, and a pair of side flaps extending in said longitudinal direction outside transversely opposite side edges of said panel, and wherein said panel comprises:

a main body extending from the front waist region to the rear waist region via the crotch region, and a pair of wings which are located in one of said front and rear waist regions, on opposite sides of said main body, each of said wings extending in the longitudinal direction from a proximal end to a distal end thereof, wherein the proximal ends of said wings are contiguous to and extend outwardly in a transverse direction of said diaper from transversely opposite edges of said main body, respectively, and wherein the distal ends of said wings are outwardly spaced in the transverse direction from the transversely opposite edges of said main body by respective folding guide zones;

said wings and the associated folding guide zones are elongated in the longitudinal direction without extending beyond a transverse center line that bisects an entire longitudinal dimension of said diaper;

each of said wings has opposite inner and outer edges, the inner edge facing an adjacent one of the transversely opposite edges of said main body while the outer edge facing away from said adjacent one of the transversely opposite edges of said main body;

each of said folding guide zones is defined between the inner edge of the respective wing and the adjacent one of the transversely opposite edges of said main body and has a stiffness less than that of said wings and the main body.

13. The diaper according to claim 12, wherein
said folding guide zones are devoid of absorbent material of said panel.

14. The diaper according to claim 13, wherein
an entire width of each of said folding guide zones, as measured in the transverse direction between the inner edge of the respective wing and the adjacent one of the transversely opposite edges of said main body, gradually increases in the longitudinal direction towards said transverse center line; and an entire width of each said wing, as measured in the transverse direction between the inner and outer edges of said wing, gradually decreases in the longitudinal direction towards said transverse center line.

15. The diaper according to claim 12, wherein
an entire width of each of said folding guide zones, as measured in the transverse direction between the inner edge of the respective wing and the adjacent one of the transversely opposite edges of said main body, gradually increases in the longitudinal direction towards said transverse center line; and an entire width of each said wing, as measured in the transverse direction between the inner and outer edges of said wing, gradually decreases in the longitudinal direction towards said transverse center line.

16. A disposable diaper, comprising a liquid-pervious topsheet, a liquid-impervious backsheet and a liquid-absorbent panel interposed between said sheets, said diaper further comprising a front waist region, a rear waist region and a crotch region extending between said waist regions in a longitudinal direction of said diaper, and a pair of side flaps extending in said longitudinal direction outside transversely opposite side edges of said panel, and wherein said panel comprises:

a main body extending from the front waist region to the rear waist region via the crotch region, and a pair of wings which are located in one of said front and rear waist regions, on opposite sides of said main body, and outwardly spaced in a transverse direction of said diaper from said main body by respective folding guide zones; and said wings and the associated folding guide zones are continuous and elongated in the longitudinal direction without extending into the other of said front and rear waist regions;

said diaper further comprises elastic members extending in said longitudinal direction, each of said elastic members having two opposite end portions one of which underlies and is directly bonded to one of said wings, and a middle portion which is located between and connects said end portions, said middle portion being attached to one of the side flaps in areas free of said panel;

said folding guide zones are devoid of absorbent material of said panel;

said main body has transversely opposite edges;

each of said wings has opposite inner and outer edges, the inner edge facing an adjacent one of the transversely opposite edges of said main body while the outer edge facing away from said adjacent one of the transversely opposite edges of said main body;

each of said folding guide zones is defined between the inner edge of the respective wing and the adjacent one of the transversely opposite edges of said main body;

an entire width of each of said folding guide zones, as measured in the transverse direction between the inner edge of the respective wing and the adjacent one of the transversely opposite edges of said main body, gradually increases in the longitudinal direction towards the crotch region; and an entire width of each said wing, as measured in the transverse direction between the inner and outer edges of said wing, gradually decreases in the longitudinal direction towards the crotch region.

17. The diaper according to claim 16, wherein an entire longitudinal extent of each of said wings is less than that of the elastic member bonded to said wing.

18. The diaper according to claim 17, wherein the entire longitudinal extent of each of said wings is less than half of that of said main body.

19. The diaper according to claim 16, further comprising:
stretchable leg elastics each extending in said longitudinal direction, spaced outwardly from said panel in said transverse direction and contractibly attached to one of said side flaps;

wherein an entirety of each of said leg elastics is not located beneath any part of said panel.

20. The diaper according to claim 19, wherein
the leg elastics attached to the same side flap generally run parallel to each other, but not parallel to the elastic member attached to said same side flap.

* * * * *